(12) United States Patent
Inayama et al.

(10) Patent No.: US 8,772,530 B2
(45) Date of Patent: Jul. 8, 2014

(54) PENTAERYTHRITOL TETRAESTER

(75) Inventors: Toshihiro Inayama, Mie (JP); Satoshi Hiyoshi, Mie (JP); Nobuhito Amemiya, Mie (JP); Shigehisa Kishimoto, Mie (JP)

(73) Assignee: KH Neochem Co., Ltd., Tokyo (JP)

( * ) Notice: Subject to any disclaimer, the term of this patent is extended or adjusted under 35 U.S.C. 154(b) by 0 days.

(21) Appl. No.: 13/813,695

(22) PCT Filed: Jun. 30, 2011

(86) PCT No.: PCT/JP2011/065109
§ 371 (c)(1),
(2), (4) Date: Feb. 1, 2013

(87) PCT Pub. No.: WO2012/026214
PCT Pub. Date: Mar. 1, 2012

(65) Prior Publication Data
US 2013/0131374 A1    May 23, 2013

(30) Foreign Application Priority Data
Aug. 24, 2010 (JP) ................ 2010-187570

(51) Int. Cl.
*C07C 69/34* (2006.01)

(52) U.S. Cl.
USPC ........................................... 560/190

(58) Field of Classification Search
USPC ........................................... 560/190
See application file for complete search history.

(56) References Cited

U.S. PATENT DOCUMENTS

| 5,395,544 A | 3/1995 | Hagihara et al. |
| 6,228,820 B1 | 5/2001 | Sakai et al. |
| 6,410,492 B1* | 6/2002 | Shimomura et al. .......... 508/485 |
| 7,045,490 B2 | 5/2006 | Shimomura et al. |
| 2003/0166478 A1 | 9/2003 | Shimomura et al. |

FOREIGN PATENT DOCUMENTS

| CN | 1315993 | 10/2001 |
| JP | 6-17073 A | 1/1994 |
| JP | 6-25682 A | 2/1994 |
| JP | 2002-129177 A | 5/2002 |
| JP | 2004-43821 A | 2/2004 |
| TW | 1235175 | 7/2005 |
| WO | 97/11933 A1 | 4/1997 |
| WO | 2012/026303 | 3/2012 |

OTHER PUBLICATIONS

China Office action, mail date is Jan. 21, 2013.
Taiwan Office action, mail date is Nov. 8, 2012.
U.S. Appl. No. 13/813,718 to Toshihiro Inayama et al., filed Feb. 1, 2013.
U.S. Appl. No. 13/813,688 to Toshihiro Inayama et al., filed Feb. 1, 2013.
Yasughiro Kawaguchi, "Recent Movement for Refrigerating Machine oil.", Lubricant Economy, Jun. 2004, pp. 17-21.
Search report from International Application No. PCT/JP2011/065109, mail date is Aug. 9, 2011.
International Preliminary Report on Patentability No. PCT/JP2011/065109, mail date is Sep. 8, 2011.

* cited by examiner

*Primary Examiner* — Yong Chu
*Assistant Examiner* — Sonya Wright
(74) *Attorney, Agent, or Firm* — Greenblum & Bernstein, P.L.C.

(57) ABSTRACT

A pentaerythritol tetraester which is a mixed ester of pentaerythritol and carboxylic acids is provided, wherein the carboxylic acids consist of isobutyric acid and 3,5,5-trimethylhexanoic acid and the molar ratio of isobutyric acid to 3,5,5-trimethylhexanoic acid in the carboxylic acids is 36/64 to 80/20. The pentaerythritol tetraester may be used in a refrigerant oil or the like which exhibits excellent miscibility with a difluoromethane refrigerant among other properties.

2 Claims, No Drawings

PENTAERYTHRITOL TETRAESTER

TECHNICAL FIELD

The invention relates to a pentaerythritol tetraester that may be used in an industrial lubricant (e.g., refrigerant oil) or the like.

BACKGROUND ART

In recent years, hydrofluorocarbons (HFC) that have zero ozone depletion potential (ODP) as well as a relatively low global warming potential (GWP) have been used as refrigerants for refrigerators. A difluoromethane refrigerant (HFC-32) has a low GWP that is about ⅓rd to ¼th of that of other refrigerants currently used (e.g., R-410A which is a mixture of difluoromethane and pentafluoroethane and R-407C which is a mixture of difluoromethane, pentafluoroethane and 1,1,1,2-tetrafluoroethane). Moreover, the difluoromethane refrigerant also has a coefficient of performance (COP) higher than that of R-410A, R-407C and the like by about 5 to 13% and therefore is a preferable refrigerant from the viewpoint of energy-saving (see Non-Patent Document 1).

Patent Document 1 discloses an ester of pentaerythritol and a fatty acid that is used as a refrigerant oil for the difluoromethane refrigerant. However, the ester disclosed in Patent Document 1 is not satisfactory in that it does not exhibit sufficient miscibility with the difluoromethane refrigerant, for example.

Patent Document 2 discloses a use of a mixed ester obtained by reacting pentaerythritol, i-nonanoic acid, and i-butyric anhydride in a molar ratio of 1:3:0.5 in the process of lubricating a ceramic-containing engine. However, Patent Document 2 does not disclose or suggest miscibility of the mixed ester with the difluoromethane refrigerant.

RELATED-ART DOCUMENTS

Patent Documents

Patent Document 1: JP 2002-129177 A
Patent Document 2: JP 2004-43821 A

Non-Patent Document

Non-Patent Document 1: Junkatsu Keizai, June 2004 (No. 460), p. 17

SUMMARY OF THE INVENTION

Technical Problem

An object of the present invention is to provide a pentaerythritol tetraester that may be used in a refrigerant oil or the like that exhibits excellent miscibility with a difluoromethane refrigerant among other properties.

Solution To Problem

The invention provides the following pentaerythritol tetraester.

[1] A pentaerythritol tetraester that is a mixed ester of pentaerythritol and carboxylic acids, the carboxylic acids consisting of isobutyric acid and 3,5,5-trimethylhexanoic acid wherein a molar ratio of isobutyric acid to 3,5,5-trimethylhexanoic acid (i.e., isobutyric acid/3,5,5-trimethylhexanoic acid ratio) is 36/64 to 80/20.

[2] The pentaerythritol tetraester according to [1], wherein the molar ratio of isobutyric acid to 3,5,5-trimethylhexanoic acid (i.e., isobutyric acid/3,5,5-trimethylhexanoic acid ratio) in the carboxylic acids is 36/64 to 67/33.

Advantageous Effects of the Invention

The invention thus provides a pentaerythritol tetraester that may be used in a refrigerant oil or the like exhibiting excellent miscibility with a difluoromethane refrigerant among other properties.

DESCRIPTION OF EMBODIMENTS

Preferred embodiments of the invention are described in detail below.

A pentaerythritol tetraester according to the invention is a mixed ester of pentaerythritol and carboxylic acids, the carboxylic acids consisting of isobutyric acid and 3,5,5-trimethylhexanoic acid wherein the molar ratio of isobutyric acid to 3,5,5-trimethylhexanoic acid (i.e., isobutyric acid/3,5,5-trimethylhexanoic acid ratio) is 36/64 to 80/20. The molar ratio of isobutyric acid to 3,5,5-trimethylhexanoic acid in the carboxylic acids is preferably 36/64 to 67/33. However, the pentaerythritol tetraester may achieve the effects of the invention even if said molar ratio does not fall within the above range. Such a pentaerythritol tetraester is also included within the scope of the invention. The term "pentaerythritol tetraester" used herein refers to a compound obtained by completely esterifying the four hydroxyl groups of pentaerythritol with four carboxylic acid molecules.

The term "mixed ester" used herein includes (i) a pentaerythritol tetraester in which the constituent carboxylic acids in one molecule consist of both isobutyric acid and 3,5,5-trimethylhexanoic acid; (ii) a mixture of an ester of pentaerythritol and isobutyric acid and an ester of pentaerythritol and 3,5,5-trimethylhexanoic acid; and (iii) a mixture of (i) and (ii).

The pentaerythritol tetraester according to the invention may comprise a pentaerythritol triester and the like as impurities.

The pentaerythritol tetraester according to the invention may be produced by reacting pentaerythritol, isobutyric acid, and 3,5,5-trimethylhexanoic acid at 120 to 250° C. for 5 to 60 hours, optionally in the presence of a catalyst.

Examples of the catalyst include mineral acids, organic acids, Lewis acids, organometals, solid acids, and the like. Specific examples of the mineral acids include hydrochloric acid, hydrofluoric acid, sulfuric acid, phosphoric acid, nitric acid, and the like. Specific examples of the organic acids include p-toluenesulfonic acid, benzenesulfonic acid, butanesulfonic acid, propanesulfonic acid, ethanesulfonic acid, methanesulfonic acid, and the like. Specific examples of the Lewis acids include boron trifluoride, aluminum chloride, tin tetrachloride, titanium tetrachloride, and the like. Specific examples of the organometals include tetrapropoxytitanium, tetrabutoxytitanium, tetrakis(2-ethylhexyloxy)titanium, and the like. Specific examples of the solid acids include a cation-exchange resin and the like.

The sum of the amount (mol) of isobutyric acid and the amount (mol) of 3,5,5-trimethylhexanoic acid is preferably larger than the amount (mol) of the hydroxyl groups of pentaerythritol by a factor of 1.1 to 1.4.

It is preferable to carry out the reaction of pentaerythritol, isobutyric acid and 3,5,5-trimethylhexanoic acid while removing from the reaction mixture the water produced during the reaction. It should be noted that isobutyric acid may be incidentally removed from the reaction mixture when the water produced during the reaction is being removed.

The water produced during the reaction may be removed from the reaction mixture by using a rectifying column attached to the reactor. In this case, the ratio of isobutyric acid included in the pentaerythritol tetraester according to the invention can be regulated by adjusting the operating conditions of the rectifying column to change the amount of vaporization of isobutyric acid.

In the reaction of pentaerythritol, isobutyric acid and 3,5,5-trimethylhexanoic acid, a solvent may be used, examples of which include hydrocarbon solvents such as benzene, toluene, xylene, hexane, heptane, isohexane, isooctane, isononane, and decane. By using the solvent, the removal of the water produced during the reaction from the reaction mixture may become more efficient and thus the reaction time may be shortened.

After completion of the reaction, the resulting pentaerythritol tetraester may optionally be purified by a method normally used in synthetic organic chemistry (e.g., washing with water and/or an alkaline aqueous solution, a treatment with activated carbon, an adsorbent, or the like, and various types of chromatography methods and distillation methods).

The pentaerythritol tetraester according to the invention exhibits excellent miscibility with a difluoromethane refrigerant, excellent low-temperature fluidity, excellent stability against hydrolysis and the like, and excellent lubricity, among other properties.

When the pentaerythritol tetraester according to the invention is used in a refrigerant oil for an air conditioner, the kinematic viscosity of the pentaerythritol tetraester at 40° C. is preferably 20 to 70 mm$^2$/sec, and more preferably 40 to 70 mm$^2$/sec. The pentaerythritol tetraester preferably has a two-phase separation temperature of −15° C. or lower. The pour point of the pentaerythritol tetraester is preferably −40.0° C. or lower, and more preferably −42.5° C. or lower.

The pentaerythritol tetraester according to the invention may be used in a refrigerant oil, as well as in an engine oil, a gear oil, grease, a plasticizer, and the like.

The refrigerant oil using the pentaerythritol tetraester according to the invention may be a refrigerant oil comprising the pentaerythritol tetraester of the invention and a lubricant additive, for example. In the refrigerant oil using the pentaerythritol tetraester according to the invention, the pentaerythritol tetraester is used as a lubricant base oil.

Examples of the lubricant additive include an antioxidant, a wear-reducing agent (e.g., anti-wear agent, anti-seize agent, and extreme pressure agent), a friction modifier, an acid scavenger, a metal deactivator, an anti-foaming agent, and the like which are usually used as lubricant additives. The amount of each additive in the refrigerant oil is preferably 0.001 to 5 wt %.

The pentaerythritol tetraester according to the invention may be used in combination with other lubricant base oils. Examples of such additional lubricant base oils include a mineral oil, a synthetic base oil, and the like.

Examples of the mineral oil include paraffinic crude oil, intermediate base crude oil, naphthenic crude oil, and the like. A refined oil obtained by purifying any of said mineral oils via distillation or the like may also be used.

Examples of the synthetic base oil include poly-α-olefins (e.g., polybutene, polypropylene, and α-olefin oligomers having 8 to 14 carbon atoms), aliphatic esters other than the pentaerythritol tetraester of the invention (e.g., fatty acid monoesters, fatty acid esters of a polyhydric alcohol, and aliphatic polybasic acid esters), aromatic esters (e.g., aromatic monoesters, aromatic esters of a polyhydric alcohol, and aromatic polybasic acid esters), polyalkylene glycols, polyvinyl ethers, polyphenyl ethers, alkylbenzenes, carbonates, synthetic naphthene, and the likes.

The pentaerythritol tetraester according to the invention has an excellent ability to dissolve lubricant additives such as a metal deactivator (e.g., benzotriazole) and a silicon-based anti-foaming agent. The lubricant additive is dissolved in the lubricant in order to prolong the lifetime of the lubricant and the system containing the lubricant, for example. The lubricant additives generally have low solubility in a pentaerythritol ester (see JP H10-259394 A). Moreover, benzotriazole has low solubility in a mineral oil and/or a synthetic oil (see JP S59-189195 A). However, benzotriazole was found to be highly soluble in any of the pentaerythritol tetraesters according to the invention. For example, solubility of Tetraester 1 (see Example 1) and Tetraester 6 (see Example 6), which both belong to the pentaerythritol tetraesters according to the invention, was at least 0.005 g/g at 25° C. The pentaerythritol tetraester according to the invention containing dissolved benzotriazole exhibits excellent low-temperature fluidity and excellent anti-wear property.

Moreover, the machines in which the pentaerythritol tetraester according to the invention has been used as a lubricant can be easily cleaned (washed) by using a detergent such as a fluorine-based detergent and an alcohol-based detergent.

EXAMPLES

The invention is further described below by providing Examples, Reference Examples, and Test Examples. However, the invention is not limited to the examples.

The nuclear magnetic resonance spectrum of each of the pentaerythritol tetraesters produced in Examples 1 to 11 and Reference Examples 1 and 2 was measured, and the molar ratio of isobutyric acid to 3,5,5-trimethylhexanoic acid was calculated by the formula shown below.

The nuclear magnetic resonance spectrum was measured by using the following instrument and method.

Measurement instrument: GSX-400 (400 MHz) manufactured by JEOL Ltd.

Measurement method: $^1$H-NMR (standard substance: tetramethylsilane; solvent: CDCl$_3$)

Isobutyric acid/3,5,5-trimethylhexanoic acid=integral value of peak X/integral value of peak Y In the above formula, peak X corresponds to the peak of the hydrogen atom of the methine group of isobutyric acid, and peak Y corresponds to the peak of the hydrogen atom of the methine group of 3,5,5-trimethylhexanoic acid.

Example 1

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 39/61 (Tetraester 1)

Kyowaad 500 manufactured by Kyowa Chemical Industry Co., Ltd. was used as an adsorbent.

Shirasagi P manufactured by Japan EnviroChemicals, Ltd. was used as activated carbon.

A reactor equipped with a Dean-Stark trap was charged with 1634 g (12.0 mol) of pentaerythritol (manufactured by Koei Perstorp, Co., Ltd.), 1979 g (22.5 mol) of isobutyric acid (manufactured by Tokyo Chemical Industry Co., Ltd.), and 5560 g (35.1 mol) of 3,5,5-trimethylhexanoic acid (manufactured by Kyowa Hakko Chemical Co., Ltd.). The mixture was degassed by nitrogen bubbling at room temperature for 30 minutes with stirring.

The mixture was stirred at 155 to 230° C. for 12.5 hours while nitrogen bubbling was further continued. After the addition of 1.3 g of tetrabutoxytitanium, the reaction mixture was stirred at 230° C. for 12 hours. After completion of the reaction, the reaction mixture was stirred at 225° C. for 1 hour under a reduced pressure of 1.1 kPa to remove unreacted carboxylic acids from the reaction product by distillation. The reaction product was washed at 77° C. for 1 hour with 2 liters of an alkaline aqueous solution containing sodium hydroxide at 2-fold molar excess relative to the acid number of the reaction product. The reaction product was then washed with 2 liters of water at 68° C. for 1 hour (three times). Next, the reaction product was stirred at 68° C. for 1 hour under a reduced pressure of 1.1 kPa with nitrogen bubbling to dry the reaction product.

After the addition of 141 g of the adsorbent (corresponding to 2 wt % of the reaction product) and 141 g of activated carbon (corresponding to 2 wt % of the reaction product), the mixture was stirred at 110° C. for 2 hours under a reduced pressure of 1.3 kPa with nitrogen bubbling, and then filtered by using a filter aid, to finally obtain 6402 g of Tetraester 1.

Example 2

Production of Pentaerythritol Tetraester in which the Molar Ratio of Isobutyric Acid to 3,5,5-trimethylhexanoic Acid (i.e., Isobutyric Acid/3,5,5-Trimethylhexanoic Acid Ratio) is 36/64 (Tetraester 2)

Tetraester 2 was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/1.73/3.07.

Example 3

Production of Pentaerythritol Tetraester in which the Molar Ratio of Isobutyric Acid to 3,5,5-trimethylhexanoic Acid (i.e., Isobutyric Acid/3,5,5-Trimethylhexanoic Acid Ratio) is 37/63 (Tetraester 3)

Tetraester 3 was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/1.78/3.02.

Example 4

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 58/42 (Tetraester 4)

Tetraester 4 was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/2.78/2.02.

Example 5

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 67/33 (Tetraester 5)

Tetraester 5 was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/3.22/1.58.

Example 6

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 76/24 (Tetraester 6)

Tetraester 6 was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/3.65/1.15.

Example 7

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 80/20 (Tetraester 7)

Tetraester 7 was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/3.84/0.96.

Example 8

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 50/50 (Tetraester 8)

Tetraester 8 was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/2.40/2.40.

Example 9

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 62/38 (Tetraester 9)

Tetraester 9 was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/2.98/1.82.

Example 10

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 64/36 (Tetraester 10)

Tetraester 10 was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/3.07/1.73.

Example 11

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 37/63 (Tetraester 11)

Tetraester 11 was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/1.80/3.00, and isooctane ("Kyowasol C-800" manufactured by Kyowa Hakko Chemical Co., Ltd.) was used as a solvent.

Reference Example 1

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 24/76 (Tetraester A)

Tetraester A was obtained in the same manner as in Example 1, except that isobutyric anhydride was used instead of isobutyric acid, and pentaerythritol, isobutyric anhydride and 3,5,5-trimethylhexanoic acid were used in a molar ratio (i.e., pentaerythritol/isobutyric anhydride/3,5,5-trimethylhexanoic acid ratio) of 1/0.5/3.

Reference Example 2

Production of Pentaerythritol Tetraester in which the Molar Ratio of Isobutyric Acid to 3,5,5-trimethylhexanoic Acid (i.e., Isobutyric Acid/3,5,5-trimethylhexanoic Acid Ratio) is 84/16 (Tetraester B)

Tetraester B was obtained in the same manner as in Example 1, except that the molar ratio of pentaerythritol, isobutyric acid and 3,5,5-trimethylhexanoic acid (i.e., pentaerythritol/isobutyric acid/3,5,5-trimethylhexanoic acid ratio) was changed to 1/4.03/0.77.

Test Example 1

Measurement of Pour Point

Pour points of Tetraesters 1 to 10, A, and B were measured in accordance with JIS K2269-1987 by using an automatic pour point measurement system "RPP-01CML" (manufactured by Rigo Co., Ltd.). The results are shown in Table 1.

Test Example 2

Measurement of Kinematic Viscosity

Kinematic viscosity of each of Tetraesters 1 to 11, A, and B at 40° C. was measured in accordance with JIS K2283:2000 by using a Cannon-Fenske viscometer. The results are shown in Table 1 and below.

Test Example 3

Measurement of Two-Phase Separation Temperature

The two-phase separation temperatures of Tetraesters 1 to 10, A, and B were measured in accordance with JIS K2211: 2009. Specifically, a pressure-resistant glass tube was charged with 0.4 g of the tetraester (Tetraester 1 to 11, A, or B) and 3.6 g of a difluoromethane refrigerant, and each of the mixtures was cooled from 30° C. at a rate of 0.5° C./min. The temperature at which the mixture was separated into two phases or became cloudy was defined as the two-phase separation temperature. The results are shown in Table 1 and below.

Test Example 4

Measurement of Solubility of Benzotriazole at 5° C.

0.15 g of benzotriazole was mixed with 4.85 g of the tetraester (Tetraester 1 to 10, A, or B), and each of the mixtures was heated at 60° C. to obtain a 3 wt % tetraester solution of benzotriazole. After allowing each of the tetraester solutions to stand at 5° C. for 40 hours, the presence or absence of precipitation was verified by visual inspection.

When no precipitation was observed, the solubility of benzotriazole (i.e., the amount (g) of benzotriazole dissolvable in 1 g of the tetraester) at 5° C. was determined to be 0.030 g/g or higher.

When precipitation was observed, the precipitate was removed by filtration (filter paper: No. 5A, manufactured by Kiriyama Glass Works Co), and the filtrate was then subjected to high-performance liquid chromatography (1200 SERIES manufactured by AGILENT; column: YMC Pack Ph A-414, 6.0 (diameter)×300 mm; mobile phase: tetrahydrofuran/0.1% phosphoric acid aqueous solution (in the ratio of 7/3); column temperature: 40° C.; flow rate: 0.7 ml/min; detection: UV (220 nm); sample concentration: 50 g/l; injection volume: 5 µl), and the solubility of benzotriazole (i.e., the amount (g) of benzotriazole dissolvable in 1 g of the tetraester) at 5° C. was determined by an absolute calibration method. The results are shown in Table 2.

Test Example 5

Measurement of Wear Scar Diameter Using the Tetraester Solutions 0.20 g of benzotriazole was mixed with 19.80 g of the tetraester (Tetraester 1 to 10, A, or B), and each of the mixtures was heated at 60° C. to obtain a 1 wt % tetraester solution of benzotriazole.

Each of the 1 wt % tetraester solutions was subjected to a wear test by using a Shell four-ball wear tester (manufactured by Shinko Engineering Co., Ltd.) (load: 200 N; rotating speed: 1200 rpm; duration: 30 minutes; temperature: 75° C.; test piece: test ball SUJ-2) to measure the wear scar diameter. The average value of the wear scar diameters on the three stationary balls in both vertical and horizontal directions was taken as the wear scar diameter. The results are shown in Table 2. In Table 2, a smaller wear scar diameter indicates better anti-wear property of the tetraester solution.

Test Example 6

Measurement of Pour Point of Tetraester Solution 1.35 g of benzotriazole was mixed with 43.65 g of the tetraester (Tetraester 1 to 10, A, or B), and each of the mixtures was heated at 60° C. to obtain a 3 wt % tetraester solution of benzotriazole.

The pour points of the 3 wt % tetraester solutions were measured in accordance with RS K2269-1987 by using an automatic pour point measurement system "RPP-01CML" (manufactured by Rigo Co., Ltd.). The results are shown in Table 2.

In Table 2, BZT indicates benzotriazole.

and a two-phase separation temperature of −20° C. which were similar to those of Example 3.

As shown in Table 2, Tetraesters 1 to 10 were highly capable of dissolving benzotriazole, the solubility of which being 0.020 g/g or higher at 5° C. The 3 wt % solutions of benzotriazole in Tetraesters 1 to 10 had a pour point of −40.0° C. or lower, and the wear scar diameters measured with the 1 wt % solutions of benzotriazole in Tetraesters 1 to 10 were 0.60 mm or less. It was thus confirmed that Tetraesters 1 to 10 exhibited excellent low-temperature fluidity and excellent anti-wear properties in the presence of benzotriazole dissolved therein.

Industrial Applicability

The present invention thus provides a pentaerythritol tetraester that may be used in a refrigerant oil or the like which exhibits excellent miscibility with a difluoromethane refrigerant among other properties.

The invention claimed is:

1. A pentaerythritol tetraester that is a mixed ester of pentaerythritol and carboxylic acids, the carboxylic acids consisting of isobutyric acid and 3,5,5-trimethylhexanoic acid wherein a molar ratio of isobutyric acid to 3,5,5-trimethylhexanoic acid (isobutyric acid/3,5,5-trimethylhexanoic acid ratio) is 36/64 to 80/20.

2. The pentaerythrutol tetraester according to claim 1, wherein the molar ratio of isobutyric acid to 3,5,5-trimethylhexanoic acid (isobutyric acid/3,5,5-trimethylhexanoic acid ratio) in the carboxylic acids is 36/64 to 67/33.

TABLE 1

| Tetraester | Isobutyric acid/ 3,5,5-trimethylhexanoic acid ratio (molar ratio) | Kinematic viscosity (mm²/sec) | Pour point (° C.) | Two-phase separation temp. (° C.) |
|---|---|---|---|---|
| A (Ref. Example 1) | 24/76 | 88.2 | −37.5 | −1 |
| 2 (Example 2) | 36/64 | 69.5 | −42.5 | −20 |
| 3 (Example 3) | 37/63 | 68.9 | −42.5 | −20 |
| 1 (Example 1) | 39/61 | 66.3 | −42.5 | −23 |
| 8 (Example 8) | 50/50 | 55.2 | −42.5 | −35 |
| 4 (Example 4) | 58/42 | 47.7 | −45.0 | −41 |
| 9 (Example 9) | 62/38 | 45.7 | −45.0 | −47 |
| 10 (Example 10) | 64/36 | 43.6 | −45.0 | ≤−50 |
| 5 (Example 5) | 67/33 | 40.1 | −45.0 | ≤−50 |
| 6 (Example 6) | 76/24 | 33.9 | −40.0 | ≤−50 |
| 7 (Example 7) | 80/20 | 30.6 | −40.0 | ≤−50 |
| B (Ref. Example 2) | 84/16 | 27.9 | −20.0 | ≤−50 |

TABLE 2

| Tetraester | Isobutyric acid/ 3,5,5-trimethylhexanoic acid ratio (molar ratio) | Solubility of BZT at 5° C. (g/g) | Wear scar diameter (mm) 1 wt % tetraester solution of BZT | Pour point (° C.) 3 wt % tetraester solution of BZT |
|---|---|---|---|---|
| A (Ref. Example 1) | 24/76 | 0.014 | 0.62 | −17.5 |
| 2 (Example 2) | 36/64 | 0.021 | 0.49 | −40.0 |
| 3 (Example 3) | 37/63 | 0.020 | 0.52 | −40.0 |
| 1 (Example 1) | 39/61 | 0.021 | 0.54 | −40.0 |
| 8 (Example 8) | 50/50 | 0.025 | 0.60 | −42.5 |
| 4 (Example 4) | 58/42 | 0.024 | 0.56 | −45.0 |
| 9 (Example 9) | 62/38 | ≥0.030 | 0.57 | −45.0 |
| 10 (Example 10) | 64/36 | ≥0.030 | 0.55 | −45.0 |
| 5 (Example 5) | 67/33 | ≥0.030 | 0.55 | −45.0 |
| 6 (Example 6) | 76/24 | ≥0.030 | 0.57 | −47.5 |
| 7 (Example 7) | 80/20 | ≥0.030 | 0.60 | −47.5 |
| B (Ref. Example 21 | 84/16 | ≥0.030 | 0.55 | −20.0 |

As shown in Table 1, Tetraesters 1 to 10 had a kinematic viscosity at 40° C. of 30.6 to 69.5 mm²/sec and a pour point of −40.0 to −45.0° C., indicating excellent low-temperature fluidity. Moreover, Tetraesters 1 to 10 had a two-phase separation temperature of −20° C. or lower, indicating excellent miscibility with the difluoromethane refrigerant. Tetraesters 1 to 5 and 8 to 10 exhibited particularly excellent low-temperature fluidity as indicated by the pour point of −42.5 to −45.0° C. Tetraester 11 had a kinematic viscosity of 68.3 mm²/sec

* * * * *